US009493586B2

(12) United States Patent
Kobayashi

(10) Patent No.: US 9,493,586 B2
(45) Date of Patent: Nov. 15, 2016

(54) METHOD FOR PRODUCING MAGNESIUM ALCOHOLATE

(71) Applicant: Nippon Soda Co., Ltd., Tokyo (JP)

(72) Inventor: Hitoshi Kobayashi, Joetsu (JP)

(73) Assignee: Nippon Soda Co., Ltd., Tokyo (JP)

( * ) Notice: Subject to any disclaimer, the term of this patent is extended or adjusted under 35 U.S.C. 154(b) by 143 days.

(21) Appl. No.: 14/350,259

(22) PCT Filed: Oct. 12, 2012

(86) PCT No.: PCT/JP2012/076502

§ 371 (c)(1),
(2) Date: Apr. 7, 2014

(87) PCT Pub. No.: WO2013/058193

PCT Pub. Date: Apr. 25, 2013

(65) Prior Publication Data

US 2014/0243190 A1 Aug. 28, 2014

(30) Foreign Application Priority Data

Oct. 19, 2011 (JP) ................................ 2011-229527

(51) Int. Cl.

*B01J 21/00* (2006.01)
*B01J 23/00* (2006.01)
*B01J 25/00* (2006.01)
*B01J 29/00* (2006.01)
*B01J 31/00* (2006.01)
*C08F 4/06* (2006.01)
*C07C 29/70* (2006.01)

(52) U.S. Cl.

CPC *C08F 4/06* (2013.01); *C07C 29/70* (2013.01)

(58) Field of Classification Search

USPC ........................................ 502/171, 100, 150
See application file for complete search history.

(56) References Cited

U.S. PATENT DOCUMENTS 1,937,284 A * 11/1933 Jerome .................... B01J 21/00 502/174
2,692,239 A * 10/1954 Hunter ..................... B01J 21/10 422/224
6,034,026 A * 3/2000 Garoff .................. C08F 110/02 502/102
8,263,520 B2 * 9/2012 Coalter, III ........... C08F 110/06 502/127
2009/0118446 A1 * 5/2009 Gulevich ............. B01J 31/0204 526/124.2

FOREIGN PATENT DOCUMENTS

| | | | |
|---|---|---|---|
| CA | 2057582 C * | 8/2000 | ............ C07C 29/68 |
| EP | 0544006 A1 | 6/1993 | |
| JP | A-03-074341 | 3/1991 | |
| JP | A-04-368391 | 12/1992 | |
| JP | A-2007-509901 | 4/2007 | |
| JP | A-2007-297371 | 11/2007 | |
| JP | A-2008-512542 | 4/2008 | |
| JP | A-2010-030924 | 2/2010 | |
| JP | A-2010-030925 | 2/2010 | |
| JP | A-2012-171957 | 9/2012 | |
| KR | 10-2010-0028934 A | 3/2010 | |
| KR | 10-2010-0028935 A | 3/2010 | |
| WO | A-2005/044873 | 5/2005 | |
| WO | A-2006/033512 | 3/2006 | |
| WO | 2012/034357 A1 | 3/2012 | |

OTHER PUBLICATIONS

International Search Report dated Jan. 8, 2013, issued in corresponding PCT Application No. PCT/JP2012/076502.

* cited by examiner

*Primary Examiner* — James McDonough
(74) *Attorney, Agent, or Firm* — Andrews Kurth Kenyon LLP

(57) ABSTRACT

The purpose of the present invention is to provide a spherical or ellipsoidal magnesium alcoholate having a narrow particle size distribution even when the particle size is small. The present invention provides a method for producing a magnesium alcoholate by adding in a portionwise manner to a reaction system and reacting, metallic magnesium, an alcohol, and at least one of a halogen or a halogen atom-containing compound in the reaction system under alcohol reflux, which is a method for producing a magnesium alcoholate characterized in that a mixture of metallic magnesium, an alcohol, and at least one of a halogen or a halogen atom-containing compound is added to the reaction system at each portionwise addition.

3 Claims, No Drawings

METHOD FOR PRODUCING MAGNESIUM ALCOHOLATE

TECHNICAL FIELD

The present invention relates to a method for producing a magnesium alcoholate used for preparing a solid catalyst component for olefin polymerization or the like.

This application is a national stage application of International Application No. PCT/JP2012/076502 filed on Oct. 12, 2012, which claims priority to Japanese Patent Application No. 2011-229527, filed Oct. 19, 2011, the content of which is incorporated herein by reference.

BACKGROUND ART

As a solid catalyst component for olefin polymerization, spherical magnesium alcoholates having an average particle diameter of 60 μm or more, a less number of fine particles, and a sufficient strength have been desired. As a method for producing such magnesium alcoholates, for example, there is a method disclosed in Patent Document 1 that the final ratio of the metallic magnesium and alcohol used in the reaction system is from 1/4 to 1/25 in mass ratio, and that particulate metallic magnesium having a diameter of not more than 500 μm and the alcohol are added continuously or intermittently in a portionwise manner to the reaction system under alcohol reflux and allowed to react for 100 to 1,200 minutes. In addition, in this method, it has been described that it is preferable to carry out the addition of each of the metallic magnesium and alcohol in 10 or more separate portions, and also in a manner so that the intervals of addition is a combination of intervals selected arbitrarily from the range of 10 to 120 minutes and the total addition time is within the range of not more than 1,200 minutes. It has been described that by using this method, particulate matter of dialkoxymagnesium having spherical or ellipsoidal particle shapes with an average particle diameter represented by $D_{50}$ in the range of 60 to 200 μm, a bulk specific gravity of 0.2 to 0.7 g/ml, numerous internal pores with pore sizes from 0.1 to 5 μm as determined by TEM observation, and a particle size distribution represented by $(D_{90}-D_{10})/D_{50}$ of not more than 1, can be obtained, and the breaking strength of the aggregated particulate matter is from 0.5 to 10 MPa. It has been described that in the synthetic reaction according to this method, the use of a catalyst is preferred, while listing iodine and the like as examples of useful catalysts, and moreover, this catalyst may be initially added collectively to the reaction system or may be added while adjusting the amount in accordance with the portionwise addition of raw materials.

Further, it has been disclosed in Patent Document 2 that by reacting metallic magnesium, an alcohol, and 0.0001 gram atom or more of a halogen or halogen-containing compound containing a halogen, relative to one gram atom of the above metallic magnesium, it is possible to produce an alkoxy group-containing magnesium compound having an average particle diameter from 1 to 300 μm and also a particle size distribution index (P) represented by the following formula (1) of $P<5.0$ which indicates a narrow particle size distribution, and which can be used as it is without particle size adjusting treatments such as pulverization and classification (formula (1): $P=D_{90}/D_{10}$, where $D_{90}$ denotes a particle diameter corresponding to the cumulative weight fraction of 90%, and $D_{10}$ denotes a particle diameter corresponding to the cumulative weight fraction of 10%). In this document, it has been described that there is no need to introduce the total amount of each of metallic magnesium, an alcohol, and a halogen and/or halogen-containing compound into a reaction tank from the beginning, and the introduction may be conducted in separate portions.

CITATION LIST

Patent Documents

Patent Document 1: Japanese Unexamined Patent Application, First Publication No. 2007-297371

Patent Document 2: Japanese Unexamined Patent Application, First Publication No. Hei 4-368391

SUMMARY OF INVENTION

Technical Problem

Among all the known magnesium alcoholates described above, although those having a particle size distribution represented by $(D_{90}-D_{10})/D_{50}$ of not greater than 1 have been known, those having an even smaller distribution of less than 0.78 have not been known, and thus the magnesium alcoholates with an even smaller particle size distribution have been desired. In addition, those having an average particle diameter represented by $D_{50}$ of less than 60 μm and a particle size distribution represented by $(D_{90}-D_{10})/D_{50}$ of not greater than 1 have not been known either, and thus the magnesium alcoholates having a small particle size distribution even when the particle size is small have also been desired.

Further, in Patent Document 1, although it has been described that the catalyst used may be added to the reaction system while adjusting the amount in accordance with the portionwise addition of the raw materials, it has been suggested that in those cases where the frequency of portionwise addition of the raw materials is low, for example, when it is about four to five times, the desired product (magnesium alcoholates having an average particle diameter represented by $D_{50}$ of 60 to 200 μm and also a particle size distribution represented by $(D_{90}-D_{10})/D_{50}$ of not greater than 1) cannot be obtained.

In addition, in Patent Document 2, it has been described that the suitable frequency of portionwise additions is 5 to 10 times, and that a method is preferred in which the total amount of an alcohol is added from the beginning and metallic magnesium is then divided into several portions and added.

Furthermore, there are neither descriptions nor suggestions, in both Patent Documents 1 and 2, on a specific method for portionwise addition, for example, the way the portionwise addition is carried out and the optimal ratio of each of the raw materials that are added in a portionwise manner.

The aim of the present invention is to provide a spherical or ellipsoidal magnesium alcoholate having a narrow particle size distribution even when the particle size is small.

Solution to Problem

As a result of intensive studies in order to solve the above problems, the inventors of the present invention found that it is possible to solve the above problems by always adding a mixture containing metallic magnesium, an alcohol, and a halogen or halogen atom-containing compound at each portionwise addition, thereby leading to completion of the present invention.

That is, the present invention relates to a method for producing a magnesium alcoholate by adding in a portionwise manner to a reaction system and reacting, metallic magnesium, an alcohol, and at least one of a halogen or a halogen atom-containing compound under alcohol reflux, which is a method for producing a magnesium alcoholate characterized in that a mixture of metallic magnesium, an alcohol, and at least one of a halogen or a halogen atom-containing compound is added to the reaction system at each portionwise addition.

In the method for producing a magnesium alcoholate according to the present invention, it is preferable that the frequency of portionwise addition of the aforementioned mixture be set to less than 10 times; it is preferable that the mass ratio of metallic magnesium and alcohol and the mass ratio of metallic magnesium and halogen or halogen atom-containing compound in the aforementioned mixture added portionwise be substantially constant at each portionwise addition; and moreover, it is preferable that the interval between the portionwise additions be constant.

Advantageous Effects of Invention

By using the method for producing a magnesium alcoholate according to the present invention, it is possible to obtain a magnesium alcoholate having an unprecedented quality in which the particle size distribution, particle diameter, and particle type are controlled.

In other words, by this production method, it is possible to produce a magnesium alcoholate as a particulate matter having a particle size distribution represented by $(D_{90}-D_{10})/D_{50}$ of less than 0.78 and a spherical or ellipsoidal particle shape, or a magnesium alcoholate in the form of a particulate matter having an average particle diameter represented by $D_{50}$ of less than 60 μm, a particle size distribution represented by $(D_{90}-D_{10})/D_{50}$ of not greater than 1, and a spherical or ellipsoidal particle shape.

By preparing a catalyst for olefin polymerization using the magnesium alcoholate obtained by this method in which the particle size distribution, particle diameter, and particle type are controlled, an olefin polymer can be obtained in which the particle size distribution, particle diameter, and particle type are controlled.

DESCRIPTION OF EMBODIMENTS

The values $D_{10}$, $D_{50}$, and $D_{90}$ used in the present invention denote the particle diameters at 10%, 50%, and 90%, in terms of cumulative particle size. That is, for example, $D_{10}$ indicates a particle diameter at the time when the particle size distribution of the particulate matter is measured and the integrated value of the mass of the particulate matter reached 10% by mass. Accordingly, $D_{50}$ denotes an intermediate value of the particle diameter of the entire particulate matter, and thus this indicates the average particle diameter.

<Method for Producing Magnesium Alcoholate>

A method for producing a magnesium alcoholate according to the present invention (production method of the present invention) is a method for producing a magnesium alcoholate by adding in a portionwise manner to a reaction system and reacting, metallic magnesium, an alcohol, and at least one of a halogen or a halogen atom-containing compound under alcohol reflux, which is characterized in that a mixture of metallic magnesium, an alcohol, and at least one of a halogen or a halogen atom-containing compound is added to the reaction system at each portionwise addition.

The metallic magnesium used in the production method of the present invention may be in any form as long as the reactivity is favorable. In other words, any of those having a granular, ribbon or powder form can be used. However, it should be noted that from the viewpoint of reactivity, the degree of oxidation at the surface of metallic magnesium particles is preferably as low as possible, and those in which magnesium oxide is formed on the surface are not preferable for use. Therefore, for example, those stored under the atmosphere of an inert gas such as nitrogen, and those having a metal surface treated with a solvent that does not adversely affect the reaction to prevent surface oxidation are preferred.

In order to set the average particle diameter of the magnesium alcoholate to be produced from 10 to 50 μm, the particle size of the used metallic magnesium is preferably not greater than 350 μm, and more preferably from 88 to 350 μm. The metallic magnesium having a particle size within this range is suitable in terms of maintaining uniform reactivity.

In addition, in order to set the average particle diameter of the magnesium alcoholate to be produced to 60 μm or greater, it is preferable to use a metallic magnesium in the form of a particulate matter having a particle size of not greater than 500 μm, and it is more preferable to use a metallic magnesium in the form of a particulate matter composed of fine particles having an average particle diameter represented by $D_{50}$ of 50 to 500 μm and a particle size distribution represented by $(D_{90}-D_{10})/D_{50}$ of not more than 2. The form of the particulate matter may be a powder form.

Any alcohol can be used as the alcohol used in the production method of the present invention, but it is preferable to use a lower alcohol of 1 to 6 carbon atoms. In particular, it is preferable to use ethanol because magnesium compounds with significantly improved catalytic performance can be obtained.

Although the purity and water content of alcohol are not limited, those with a low water content are preferred. More specifically, it is preferable to use an alcohol having a water content of not more than 1%, and it is more preferable to use an alcohol having a water content of not more than 2,000 ppm. When an alcohol with a high water content is used, magnesium hydroxide tends to form easily on the surface of metallic magnesium. Further, in order to obtain a magnesium alcoholate having a more favorable morphology, the water content in an alcohol is preferably as low as possible, and in general, it is preferably not more than 200 ppm.

The ratio of metallic magnesium and alcohol used at the time of completing the addition of the entire amount of raw materials to the reaction system is preferably from 1/4 to 1/25 in terms of mass ratio. By setting the amount of alcohol to not less than 4 relative to the amount of metallic magnesium, the reaction can be allowed to proceed sufficiently, the remaining of unreacted magnesium can be suppressed, and the particle diameter can be controlled easily to achieve the target value. In addition, by setting the amount of alcohol to not more than 25 relative to the amount of metallic magnesium, the amount of alcohol incorporated in the product formed in the reaction (particulate products are mainly formed) can be reduced. As a result, it is possible to suppress the number of voids generated when the alcohol in the product is removed by evaporation by a drying treatment, and to prevent the bulk specific gravity from becoming too small.

Although the type of halogen used in the production method of the present invention is not particularly limited, chlorine, bromine, or iodine is preferred, and in particular, iodine is suitably used.

In addition, there is no limitation on the type of halogen atom-containing compound used in the production method of the present invention either, and any compounds can be used as long as they are compounds containing a halogen atom within the chemical formula thereof. More specifically, examples thereof include $MgCl_2$, Mg(OEt)Cl, Mg(OEt)I, $MgBr_2$, $CaCl_2$, NaCl, and KBr, and among these, it is preferable to use $MgCl_2$ or $MgI_2$. The state, shape, particle size or the like of the halogen or halogen atom-containing compound added to the reaction system are not particularly limited, and any of those may be selected. For example, those in the form of a solution dissolved in an alcohol-based solvent such as ethanol can be used.

The amount of halogen or halogen atom-containing compound used in the production method of the present invention is not particularly limited as long as the amount is sufficient for the reaction with metallic magnesium and alcohol, but is preferably not less than 0.0001 gram atom, more preferably not less than 0.0005 gram atom, and even more preferably not less than 0.001 gram atom, relative to 1 gram atom of metallic magnesium, at the time when the addition of the entire amount of raw materials to the reaction system is completed. The halogen or halogen atom-containing compound acts as a catalyst for the reaction with metallic magnesium and alcohol, and it is preferable to adjust the total amount added and the amount added at the time of each portionwise addition to the reaction system in accordance with the portionwise addition of other raw materials.

In the present invention, each of the halogen and halogen atom-containing compound may be used alone, or two or more types thereof may be used in combination. In addition, it is also possible to use a halogen and a halogen atom-containing compound concurrently. When used in combination, at the time when the addition of the entire amount of raw materials to the reaction system is completed, the amount of total halogen in the reaction system is preferably not less than 0.0001 gram atom, more preferably not less than 0.0005 gram atom, and even more preferably not less than 0.001 gram atom, relative to 1 gram atom of metallic magnesium.

The upper limit for the use amount of halogen and/or halogen atom-containing compound added to the reaction system is not particularly limited, but is preferably less than 0.06 gram atom, relative to 1 gram atom of metallic magnesium.

The raw materials such as metallic magnesium, alcohol, and at least one of a halogen or a halogen atom-containing compound are divided into two or more portions and added to the reaction system. The portionwise addition of raw materials to the reaction system is conducted under the reflux of an alcohol-based solvent, preferably the same alcohol as the raw material. In the production method of the present invention, the mixture added in a portionwise manner must contain all three types of materials, that is, metallic magnesium, an alcohol, and at least one of a halogen or a halogen atom-containing compound. By newly adding, not only metallic magnesium and an alcohol, but also a halogen or halogen atom-containing compound to the reaction system at each portionwise addition, the particle density (apparent specific gravity) can be increased, and moreover, the amount of amorphous fine particles can be reduced, and accompanied with this, the yield of the product can be increased. Although the frequency of portionwise addition of the aforementioned mixture to the reaction system is not particularly limited as long as it is not less than twice, the addition is preferably conducted by dividing the mixture into 2 or more portions but less than 10 portions, and more preferably it is conducted by dividing the mixture into 2 to 5 portions.

The mixture added to the reaction system at the time of portionwise addition may be any one of those containing all of metallic magnesium, an alcohol and at least one of a halogen or a halogen atom-containing compound. That is, in the aforementioned mixture, the mass ratio of metallic magnesium and alcohol and the mass ratio of metallic magnesium and halogen and/or halogen atom-containing compound are not particularly limited, and may be different at each portionwise addition, or the mixtures having the same composition may be added at the time of all the portionwise additions. Further, the portionwise addition may be performed with a material ratio different from the final addition ratio (the ratio between the total added amounts to the reaction system). For example, it is possible to increase the ratio of metallic magnesium in the early stage of the reaction from the final addition ratio and decrease the ratio of metallic magnesium added in the later stage. In the production method of the present invention, it is preferable to set the mass ratio of metallic magnesium and alcohol and the mass ratio of metallic magnesium and halogen or halogen atom-containing compound in the aforementioned mixture that is added in a portionwise manner to be substantially constant at each portionwise addition.

Further, the amount of mixture added to the reaction system in one portionwise addition is also not particularly limited, and may be different at each portionwise addition, or substantially the same amount of mixture may be added to the reaction system at each portionwise addition.

For example, the addition may be conducted by sequentially increasing the added amount. In the production method of the present invention, it is preferable to add a constant amount of mixture every time.

In the production method of the present invention, it is preferable to add the raw materials so that the following synthetic reaction is allowed to proceed only after the primary particles of the dialkoxymagnesium produced in the reaction system deposit on the dialkoxymagnesium that is already present in the system. The interval of the portionwise addition differs depending on other conditions such as the size of the reaction apparatus and the temperature, but is preferably adjusted so as to be an interval of 10 to 120 minutes. In other words, it is preferable to add the next raw material at a stage where dialkoxymagnesium is produced by the reaction and the generation of $H_2$ is almost completed (stage where unreacted metallic magnesium is substantially absent) after the portionwise addition in the previous stage. It is preferable to add, at the time point where the reaction of added magnesium is almost completed, the next portion of magnesium, and it is preferable to add, so that the final ratio of metallic magnesium and alcohol be within the range from 1/4 to 1/25 in terms of weight ratio.

Note that in order to allow the reaction to proceed smoothly, it is preferable to react metallic magnesium in a relatively small amount of alcohol at an early stage of the reaction, and to adjust the concentration by further adding alcohol after adding all of metallic magnesium.

The interval of the portionwise addition of the aforementioned mixture to the reaction system is not particularly limited, and can be adjusted as appropriate by taking into consideration the amount, composition, or the like of the mixture that is added in a portionwise manner. In the production method of the present invention, it is preferable to sequentially add at a constant interval.

By the addition interval of the mixture described above, the $D_{50}$ value of the obtained magnesium alcoholate can be controlled. For example, it is possible to obtain a magnesium alcoholate having a small particle size by shortening the addition interval, and it is possible to obtain a magnesium alcoholate having a large particle size by increasing the addition interval, respectively.

Although the total reaction time depends on the scale thereof, the time point at which the reaction is completed can be determined by the completion of hydrogen generation.

After the final addition of the aforementioned mixture, it is preferable to further conduct an aging process at a temperature from 70° C. to the reflux temperature of the solvent, following the completion of hydrogen generation, to thereby stabilize the produced particles. The aging time can be altered as appropriate in accordance with the intended particle diameter, particle size distribution and bulk specific gravity of magnesium alcoholate. The reaction temperature at the time of aging may be from 70° C. to the reflux temperature of the solvent, and the stirring speed is from 50 to 500 rpm, and the reaction temperature and the stirring speed can be selected in accordance with the intended particle diameter, particle size distribution and bulk specific gravity of magnesium alcoholate.

More specifically, by reducing the stirring speed (the transfer rate of the reaction solution), the particle diameter of magnesium alcoholate can be increased, and by increasing the stirring speed, the particle diameter of magnesium alcoholate can be decreased.

<Magnesium Alcoholate>

According to the production method of the present invention, a magnesium alcoholate in which the particle size distribution, particle diameter and particle type are controlled can be produced. For example, it is possible to produce a magnesium alcoholate in the form of particulate matter having the $D_{50}$ particle diameter within the range from 10 to 200 μm, in particular, particulate matter having a large particle diameter from 80 to 200 μm which enables the omission of a pelleting process at the time of molding the olefin polymers produced when used in a polymerization catalyst.

In addition, according to the production method of the present invention, a magnesium alcoholate can be produced as particulate matter having a relatively uniform particle diameter distribution. For example, it is possible to obtain particulate matter of a magnesium alcoholate having a particle size distribution represented by $(D_{90}-D_{10})/D_{50}$ of not more than 1, preferably less than 0.78. In particular, even when the $D_{50}$ particle size is less than 60 μm, it is possible to make the aforementioned value of particle size distribution to less than 1.

That is, the magnesium alcoholate according to the present invention is characterized as being a particulate matter with a particle size distribution represented by $(D_{90}-D_{10})/D_{50}$ of less than 0.78 and having a spherical or ellipsoidal particle shape. In addition, as another aspect, the magnesium alcoholate according to the present invention is characterized as being a particulate matter having an average particle diameter represented by $D_{50}$ of less than 60 μm, a particle size distribution represented by $(D_{90}-D_{10})/D_{50}$ of not more than 1, and a spherical or ellipsoidal particle shape.

Further, the magnesium alcoholate of the present invention may be composed of porous aggregates of the spherical, ellipsoidal, scale-like, or needle-like primary particles of magnesium alcoholate having a particle diameter of 1 to 10 μm, and preferably does not substantially contain particles having a particle diameter of 10 μm or less. The pores present inside the particulate matter and having a pore diameter of 0.1 to 5 μm as observed by a transmission electron microscope (TEM) are thought to be those composed of gaps between the particles that are formed when the primary particles aggregated as described above. When these gaps between the particles become 10 μm or greater, there are some cases where the bonds between the primary particles are weak, thereby making the strength of the particulate matter insufficient.

As described above, the magnesium alcoholate of the present invention is a particulate matter having a narrow particle size distribution and a spherical or ellipsoidal particle shape even when the particle size is small. For this reason, in particular, it can be used suitably as a solid catalyst component for olefin polymerization.

In order to prepare a catalyst for olefin polymerization by using the magnesium alcoholate of the present invention as a starting material, the magnesium alcoholate (particulate matter of dialkoxymagnesium) is brought into contact with a halide of tetravalent titanium and an electron donating compound by a known method to produce a catalyst component, and then an organic aluminum compound is allowed to act thereon. Examples of the halide of tetravalent titanium include titanium tetrachloride and alkoxy titanium halides. Examples of the electron donating compounds include alcohols, ethers, esters, and organic silicon compounds such as alkoxysilane. Examples of the aluminum compounds include triethylaluminum and diethylalminum chloride.

EXAMPLES

A more detailed description of the present invention is presented below based on a series of examples, although the present invention is in no way limited by these examples.

Example 1

A reflux condenser connected with an integrating-type gas meter, a thermometer, a dropping funnel for ethanol, as well as a nitrogen inlet tube interposed with a gas flow meter were installed onto a 500 ml four-necked flask equipped with a stirrer. After sufficiently replacing the inside of the reaction system with nitrogen, 60 g of anhydrous ethanol (water content: 200 ppm) and 0.4 g of iodine were charged and dissolved therein. 6.1 g of metallic magnesium (particle size: 300 to 149 μm) was charged thereinto, and under stirring at a stirring intensity of $2.60\times10^{11}$ $rpm^3\cdot mm_2$, the temperature was raised up to the reflux temperature of the alcohol in an oil bath. The reaction was stabilized within 10 minutes from the charging of the metallic magnesium, and thereafter, 40 g of ethanol, 6.1 g of metallic magnesium and 0.3 g of iodine were charged at a time every 10 minutes and in three separate portions to allow the reaction to continue. The total amount of the charged metallic magnesium was 24.4 g, and the amount of ethanol used at this point was 180 g. Further, when 183 g of ethanol of the same quality as that of the one used earlier was added dropwise over 1 hour to allow the ageing reaction to continue until no hydrogen gas was detectable in the exhaust gas, it took 8 hours in total from the initial charging.

The ethanol/metallic magnesium ratio (mass ratio of the total amount of ethanol and the total amount of metallic magnesium that were charged into the reaction system) was 16/1. After the completion of the reaction, the liquid in the reaction system was dried under reduced pressure in a rotary evaporator to obtain 107 g (yield: 94%) of magnesium ethylate. As a result of observing the thus obtained magnesium ethylate using a scanning electron microscope (JSM-5300 manufactured by JEOL Ltd. DATUM Solution Business Operations) at 1.000-fold magnification with an accelerating voltage of 20 kV, subspherical particles made of those, each one of which is a strip-like particle, that were densely overlapping were obtained, although the particle surface was smooth. The degree of sphericity (S) as determined from the pictures taken was 1.01. When the particle size distribution was measured using a laser diffraction type particle size distribution measuring apparatus (HELOS & RODOS manufactured by Sympatec GmbH), $D_{50}$ was 40.98 µm, $D_{10}$ was 25.14 µm, $D_{90}$ was 55.58 µm, and the particle size distribution had a narrow distribution width of 0.743. In addition, the measurement result of bulk specific gravity (looseness) (apparent specific gravity) was 0.301 g/ml. The above results are summarized and shown in Table 2.

Examples 2 to 7

The measurements in these Examples were carried out in the same manner as in Example 1 with the exception that the numerical values corresponding to each of the conditions used in Example 1 were changed to the numerical values set forth in Table 1. The results are summarized and shown in Table 2. In Table 1, "Mg" represents magnesium, "I" represents iodine, and "frequency" of the "portionwise addition" represents the frequency of portionwise addition, respectively.

TABLE 1

| | Total amount used (g) | | Amount of portionwise addition (g) | | | | | Stirring intensity | Addition interval |
|---|---|---|---|---|---|---|---|---|---|
| | | | Charging | | Portionwise addition | | | | |
| | Mg | I | Mg | I | Mg | I | Frequency | ($rpm^3 \cdot mm_2$) | (minutes) |
| Ex. 1 | 24.4 | 1.3 | 6.1 | 0.4 | 6.1 | 0.3 | 3 | $2.60 \times 10^{11}$ | 10 |
| Ex. 2 | 18.4 | 1.3 | 6.1 | 0.4 | 4.1 | 0.3 | 3 | $2.60 \times 10^{11}$ | 10 |
| Ex. 3 | 24.4 | 1.5 | 6.1 | 0.6 | 6.1 | 0.3 | 3 | $2.60 \times 10^{11}$ | 15 |
| Ex. 4 | 24.4 | 1.5 | 6.1 | 0.6 | 6.1 | 0.3 | 3 | $1.60 \times 10^{11}$ | 15 |
| Ex. 5 | 24.4 | 1.5 | 6.1 | 0.6 | 6.1 | 0.3 | 3 | $1.60 \times 10^{11}$ | 20 |
| Ex. 6 | 24.4 | 1.98 | 6.1 | 0.6 | 6.1 | 0.46 | 3 | $6.75 \times 10^{10}$ | 20 |
| Ex. 7 | 24.4 | 1.98 | 6.1 | 0.6 | 6.1 | 0.46 | 3 | $6.75 \times 10^{10}$ | 20 |

TABLE 2

| | Product yield (%) | $D_{50}$ (µm) | Particle size distribution | Apparent specific gravity (g/ml) |
|---|---|---|---|---|
| Example 1 | 93.8 | 40.98 | 0.743 | 0.301 |
| Example 2 | 93.2 | 46.64 | 0.536 | 0.311 |
| Example 3 | 94.5 | 48.49 | 0.501 | 0.295 |
| Example 4 | 96.3 | 51.75 | 0.566 | 0.291 |
| Example 5 | 94.8 | 67.77 | 0.511 | 0.301 |
| Example 6 | 93.5 | 73.83 | 0.562 | 0.31 |
| Example 7 | 94.0 | 71.34 | 0.487 | 0.301 |

Example 8

A reflux condenser connected with an integrating-type gas meter, a thermometer, a dropping funnel for ethanol, as well as a nitrogen inlet tube interposed with a gas flow meter were installed onto a 500 ml four-necked flask equipped with a stirrer. After sufficiently replacing the inside of the reaction system with nitrogen, 100 g of anhydrous ethanol (water content: 200 ppm) and 0.6 g of iodine were charged and dissolved therein. 8.1 g of metallic magnesium (particle size: 300 to 149 µm) was charged thereinto, and under stirring, the temperature was raised up to the reflux temperature of the alcohol in an oil bath. Since the reaction was stabilized within 10 minutes from the charging of the metallic magnesium, 10 g of ethanol, 4.1 g of metallic magnesium, and 0.3 g of iodine were additionally added after 10 minutes from the point of charging the metallic magnesium, and after another 10 minutes, 40 g of ethanol, 7.1 g of metallic magnesium, and 0.2 g of iodine were additionally added, and after another 10 minutes, 30 g of ethanol, 5.1 g of metallic magnesium, and 0.1 g of iodine were additionally added, thereby dividing the addition into three separate portions to allow the reaction to continue. The total amount of the charged metallic magnesium was 24.4 g, and the amount of ethanol used at this point was 180 g. Further, when 183 g of ethanol of the same quality as that of the one used earlier was added dropwise over 1 hour to allow the ageing reaction to continue until no hydrogen gas was detectable in the exhaust gas, it took 5 hours in total from the initial charging.

The ethanol/metallic magnesium ratio was 15/1. After the completion of the reaction, the liquid in the reaction system was dried under reduced pressure in a rotary evaporator to obtain 105 g (yield: 92.1%) of magnesium ethylate. When the particle size distribution was measured in the same manner as in Example 1, $D_{50}$ was 48.34 µm, $D_{10}$ was 36.36 µm, $D_{90}$ was 60.12 µm, and the particle size distribution had a narrow distribution width of 0.492. In addition, the measurement result of bulk specific gravity (looseness) was 0.288 g/ml.

Example 9

A reflux condenser connected with an integrating-type gas meter, a thermometer, a dropping funnel for ethanol, as well as a nitrogen inlet tube interposed with a gas flow meter were installed onto a 500 ml four-necked flask equipped with a stirrer. After sufficiently replacing the inside of the reaction system with nitrogen, 60 g of anhydrous ethanol (water content: 200 ppm) and 0.4 g of iodine were charged and dissolved therein. 6.1 g of metallic magnesium (particle size: 210 to 149 µm) was charged thereinto, and under stirring, the temperature was raised up to the reflux temperature of the alcohol in an oil bath. Since the reaction was stabilized within 10 minutes from the charging of the metallic magnesium, 40 g of ethanol, 6.1 g of metallic magnesium, and 0.3 g of iodine were additionally added after 10 minutes from the point of charging the metallic magnesium, and after another 15 minutes, 40 g of ethanol, 6.1 g of metallic magnesium, and 0.3 g of iodine were additionally added, and after another 5 minutes, 40 g of ethanol, 6.1 g of metallic magnesium, and 0.3 g of iodine were additionally added, thereby dividing the addition into three separate portions to allow the reaction to continue.

The total amount of the charged metallic magnesium was 24.4 g, and the amount of ethanol used at this point was 180 g. Further, when 183 g of ethanol of the same quality as that of the one used earlier was added dropwise over 1 hour to allow the ageing reaction to continue until no hydrogen gas was detectable in the exhaust gas, it took 5 hours in total from the initial charging.

The ethanol/metallic magnesium ratio was 15/1. After the completion of the reaction, the liquid in the reaction system was dried under reduced pressure in a rotary evaporator to obtain 107 g (yield: 93.8%) of magnesium ethylate. When the particle size distribution was measured in the same manner as in Example 1, $D_{50}$ was 57.1 μm, $D_{10}$ was 43.03 μm, $D_{90}$ was 71.06 μm, and the particle size distribution had a narrow distribution width of 0.491. In addition, the measurement result of bulk specific gravity (looseness) was 0.319 g/ml.

Examples 10 to 27

The measurements in these Examples were carried out in the same manner as in Example 1 with the exception that the numerical values corresponding to each of the conditions used in Example 1 were changed to the numerical values set forth in Table 3. The results are summarized and shown in Table 4.

In Example 17, the amount of ethanol used was 183 g at the time of charging and was 120 g at the time of each portionwise addition, the amount of ethanol at the point where all of the charging had been completed was 543 g, and another 549 g was further added as a diluent.

TABLE 3

| | Metallic Mg apparent specific gravity (g/ml) | Total amount used (g) | | Amount of portionwise addition (g) | | | | | Stirring intensity | Addition interval |
|---|---|---|---|---|---|---|---|---|---|---|
| | | | | Charging | | Portionwise addition | | | | |
| | | Mg | I | Mg | I | Mg | I | Frequency | (rpm³ · mm₂) | (minutes) |
| Ex. 10 | 0.838 | 24.4 | 1.3 | 6.1 | 0.4 | 6.1 | 0.3 | 3 | $2.60 \times 10^{11}$ | 10 |
| Ex. 11 | 0.838 | 24.4 | 1.3 | 6.1 | 0.4 | 6.1 | 0.3 | 3 | $6.75 \times 10^{10}$ | 10 |
| Ex. 12 | 0.838 | 24.4 | 1.3 | 6.1 | 0.4 | 6.1 | 0.3 | 3 | $2.60 \times 10^{11}$ | 20 |
| Ex. 13 | 0.838 | 24.4 | 1.3 | 6.1 | 0.4 | 6.1 | 0.3 | 3 | $6.75 \times 10^{10}$ | 20 |
| Ex. 14 | 0.855 | 24.4 | 1.3 | 6.1 | 0.4 | 6.1 | 0.3 | 3 | $2.60 \times 10^{11}$ | 10 |
| Ex. 15 | 0.855 | 24.4 | 1.3 | 6.1 | 0.4 | 6.1 | 0.3 | 3 | $6.75 \times 10^{10}$ | 10 |
| Ex. 16 | 0.855 | 24.4 | 1.98 | 6.1 | 0.6 | 6.1 | 0.46 | 3 | $2.60 \times 10^{11}$ | 15 |
| Ex. 17 | 0.855 | 73.2 | 5.94 | 18.3 | 1.8 | 18.3 | 1.38 | 3 | $6.75 \times 10^{10}$ | 15 |
| Ex. 18 | 0.855 | 24.4 | 1.3 | 6.1 | 0.4 | 6.1 | 0.3 | 3 | $2.60 \times 10^{11}$ | 25 |
| Ex. 19 | 0.769 | 24.4 | 1.3 | 6.1 | 0.4 | 6.1 | 0.3 | 3 | $2.60 \times 10^{11}$ | 10 |
| Ex. 20 | 0.769 | 24.4 | 1.3 | 6.1 | 0.4 | 6.1 | 0.3 | 3 | $1.60 \times 10^{11}$ | 10 |
| Ex. 21 | 0.769 | 24.4 | 1.3 | 6.1 | 0.4 | 6.1 | 0.3 | 3 | $2.60 \times 10^{11}$ | 15 |
| Ex. 22 | 0.769 | 24.4 | 1.3 | 6.1 | 0.4 | 6.1 | 0.3 | 3 | $1.60 \times 10^{11}$ | 15 |
| Ex. 23 | 0.769 | 24.4 | 1.3 | 6.1 | 0.4 | 6.1 | 0.3 | 3 | $1.60 \times 10^{11}$ | 15 |
| Ex. 24 | 0.769 | 24.4 | 1.3 | 6.1 | 0.4 | 6.1 | 0.3 | 3 | $2.60 \times 10^{11}$ | 20 |
| Ex. 25 | 0.769 | 24.4 | 1.3 | 6.1 | 0.4 | 6.1 | 0.3 | 3 | $1.60 \times 10^{11}$ | 20 |
| Ex. 26 | 0.769 | 24.4 | 1.3 | 6.1 | 0.4 | 6.1 | 0.3 | 3 | $6.75 \times 10^{10}$ | 20 |
| Ex. 27 | 0.769 | 24.4 | 1.3 | 6.1 | 0.4 | 6.1 | 0.3 | 3 | $6.75 \times 10^{10}$ | 25 |

TABLE 4

| | Product yield (%) | $D_{50}$ (μm) | Particle size distribution | Apparent specific gravity (g/ml) |
|---|---|---|---|---|
| Example 10 | 94.3 | 57.1 | 0.458 | 0.27 |
| Example 11 | 94.6 | 67.51 | 0.459 | 0.302 |
| Example 12 | 95.1 | 67.62 | 0.467 | 0.303 |
| Example 13 | 96.3 | 76.58 | 0.539 | 0.292 |
| Example 14 | 93.2 | 46.64 | 0.536 | 0.311 |
| Example 15 | 96.8 | 57.75 | 0.466 | 0.27 |
| Example 16 | 88.7 | 55.74 | 0.807 | 0.29 |
| Example 17 | 93.1 | 64.26 | 0.523 | 0.3 |
| Example 18 | 97.3 | 59.19 | 0.513 | 0.26 |
| Example 19 | 94.3 | 45.15 | 0.553 | 0.302 |
| Example 20 | 94.3 | 50.54 | 0.578 | 0.303 |
| Example 21 | 99.11 | 48.72 | 0.485 | 0.28 |
| Example 22 | 96.3 | 51.75 | 0.566 | 0.291 |
| Example 23 | 94.2 | 52.9 | 0.571 | 0.293 |
| Example 24 | 93.8 | 51.2 | 0.576 | 0.32 |
| Example 25 | 95.7 | 54.43 | 0.521 | 0.296 |
| Example 26 | 92 | 58.63 | 0.481 | 0.283 |
| Example 27 | 93.1 | 60.33 | 0.521 | 0.298 |

Comparative Example 1

Using the same apparatus as in Example 1, 181 g of anhydrous ethanol, 1.3 g of iodine, and 24.4 g of metallic magnesium (350 to 210 μm) were charged thereto, and the temperature was raised under alcohol reflux to initiate the reaction. The aging reaction was conducted for 5 hours to complete the reaction. The particles obtained by drying had a degree of sphericity (S) of 1.25, $D_{50}$ was 46.69 μm, $D_{10}$ was 24.23 μm, $D_{90}$ was 70.87 μm, the particle size distribution had a wide distribution width of 0.999, the particle surface was not dense, and the degree of sphericity was somewhat low with a large number of irregularities. In addition, the bulk specific gravity (looseness) was 0.203 g/ml.

Comparative Example 2

A 500 ml four-necked, round-bottom flask was mounted with a stirring device, a dropping funnel and a thermometer, and 61 g of ethanol, 1.3 g of iodine and 6.1 g of granular metallic magnesium were first charged thereto under a stream of nitrogen, and were heated to reflux at a bath temperature of 80° C. After 10 minutes, 40 g of ethanol and 6.1 g of metallic magnesium were additionally added, and after another 10 minutes, 40 g of ethanol and 6.1 g of metallic magnesium were additionally added, and after another 10 minutes, 40 g of ethanol and 6.1 g of metallic magnesium were additionally added, and after another 10 minutes, 185 g of ethanol was added dropwise over 1 hour, followed by 5 hours of aging process to complete the reaction. Then, after being cooled to room temperature, ethanol was removed by evaporation under reduced pressure, followed by drying to obtain 79.9 g of magnesium ethylate (yield: 75.9%), which was the intended product.

The thus obtained particles had a $D_{50}$ of 46.69 μm, a $D_{10}$ of 24.23 μm, and a $D_{90}$ of 70.87 μm, and the particle size distribution had a wide distribution of 0.999. The bulk specific gravity (looseness) was a small value of 0.203 g/ml.

INDUSTRIAL APPLICABILITY

By using the method for producing a magnesium alcoholate according to the present invention, it is possible to obtain a magnesium alcoholate having an unprecedented quality in which the particle size distribution, particle diameter, and particle type are controlled.

By preparing a catalyst for olefin polymerization using the magnesium alcoholate obtained by this method, an olefin polymer can be obtained in which the particle size distribution, particle diameter, and particle type are controlled. From the above results, the present invention is extremely useful industrially.

The invention claimed is:

1. A magnesium alcoholate which is a particulate matter comprising a particle size distribution represented by (D90–D10)/D50 of 1.0 or less and a spherical or ellipsoidal particle shape, wherein the particulate matter is composed of porous aggregates of spherical, ellipsoidal, scale-like or needle-like primary particles of magnesium alcoholate having a particle diameter of 1 to 10 μm.

2. The magnesium alcoholate which is a particulate matter according to claim 1, wherein the pores presented inside the particulate matter have a pore diameter of 0.1 to 5 μm.

3. The magnesium alcoholate which is a particulate matter according to claim 1, wherein the particulate matter does not contain secondary particles having a particle diameter of 10 μm or less.

* * * * *